United States Patent [19]

Bell et al.

[11] 3,968,121

[45] July 6, 1976

[54] 1,2-DIPHENYL-4,5,6,7-TETRAHYDROINDOLES

[75] Inventors: Malcolm R. Bell, East Greenbush; Andrew W. Zalay, Albany, both of N.Y.

[73] Assignee: Sterling Drug Inc., New York, N.Y.

[22] Filed: Jan. 13, 1975

[21] Appl. No.: 540,550

Related U.S. Application Data

[62] Division of Ser. No. 347,620, April 4, 1973, Pat. No. 3,898,246, which is a division of Ser. No. 156,068, June 23, 1971, Pat. No. 3,799,943.

[52] U.S. Cl. .................. 260/326.13 R; 260/243 B; 260/247.2 B; 260/247.5 R; 260/268 BC; 260/293.61; 260/326.14 R; 260/326.15 R; 260/326.16; 260/326.5 R; 260/473 R; 260/592; 424/246; 424/248; 424/250; 424/267; 424/274

[51] Int. Cl.$^2$............... C07D 209/08; C07D 209/12

[58] Field of Search............... 260/326.13 R, 326.16

[56] References Cited

UNITED STATES PATENTS

| 3,799,943 | 3/1974 | Bell et al........................ 260/326.16 |
| 3,898,246 | 8/1975 | Bell et al........................ 260/326.16 |

OTHER PUBLICATIONS

Bell et al. *J. Med. Chem.* 1970 (July) pp. 664–668.

*Primary Examiner*—Nicholas S. Rizzo
*Assistant Examiner*—Mary C. Vaughn
*Attorney, Agent, or Firm*—Frederik W. Stonner; B. Woodrow Wyatt

[57] ABSTRACT

This invention relates to novel 1-[4-($R_1R_2$N-$C_nH_{2n}$-O)phenyl]-5-$R_4$-2-(4-$R_3$-phenyl)indoles having antifertility and hypocholesterolemic activities and to novel intermediates for their preparation.

7 Claims, No Drawings

1,2-DIPHENYL-4,5,6,7-TETRAHYDROINDOLES

This a division, of application Ser. No. 347,620, filed Apr. 4, 1973, now U.S. Pat. No. 3,898,246, issued Aug. 5, 1975, in turn a division of application Ser. No. 156,068, filed June 23, 1971, now U.S. Pat. No. 3,799,943, issued Mar. 26, 1974.

The invention relates to novel derivatives of 1,2-diphenylindoles (formula I below) and to novel intermediates for their preparation.

In one aspect of the invention there are provided novel 1-[4-($R_1R_2$N-$C_nH_{2n}$-O)phenyl]-5-$R_4$-2-(4-$R_3$-phenyl)indoles having the formula

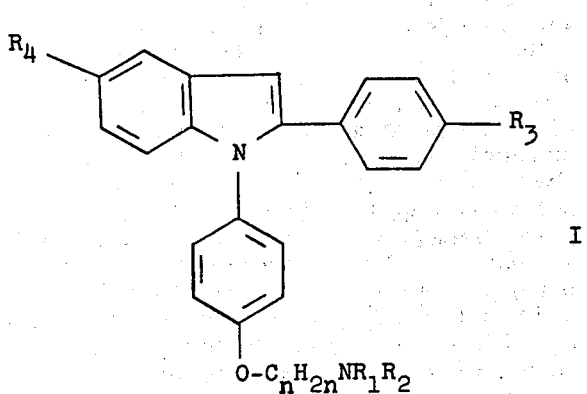

where $R_1$ and $R_2$, which can be the same or different, are lower-alkyl, or $R_1$ and $R_2$ together with the nitrogen form a heterocyclic ring selected from 1-pyrrolidyl, 1-piperidyl, 1-piperazinyl, 4-lower-alkyl-1-piperazinyl, 4-phenyl-1-piperazinyl, 4-morpholinyl and 4-thiomorpholinyl and such rings substituted on carbon by from one to three lower-alkyl substituents, and n is an integer from 2 to 4 inclusive; $R_3$ is hydrogen, lower-alkyl, lower-alkoxy or halo; and $R_4$ is hydrogen, lower-alkyl, lower-alkoxy, benzoyloxy and hydroxy.

A preferred group of compounds of the invention are the compounds of formula I where $R_4$ is hydrogen or methoxy. A particularly preferred group of compounds of the invention are the compounds of formula I where $R_4$ is hydrogen or methoxy and n is the integer 2.

In another aspect of this invention there are provided the compounds having the formula

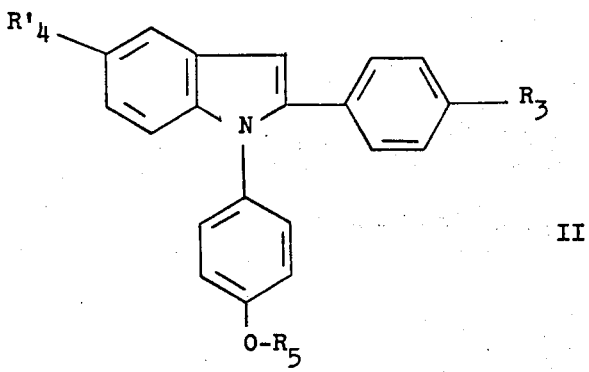

where $R_3$ is hydrogen, lower-alkyl, lower-alkoxy or halo; $R'_4$ is hydrogen, lower-alkyl, lower-alkoxy or benzoyloxy, and $R_5$ is hydrogen or benzyl.

In still another aspect of this invention there are provided the compounds of the formula

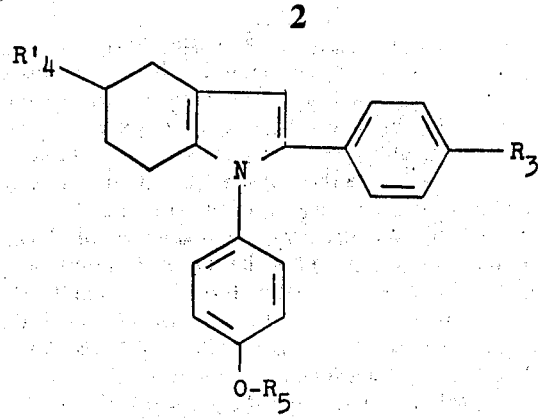

where $R_3$ is hydrogen, lower-alkyl, lower-alkoxy or halo; $R'_4$ is hydrogen, lower-alkyl, lower-alkoxy or benzoyloxy; and $R_5$ is hydrogen or benzyl.

Throughout the specification the term "lower-alkyl" and "lower-alkoxy" mean such groups having from one to four carbon atoms which can be straight or branched as illustrated by methyl, ethyl, propyl, isopropyl, butyl, isobutyl, tertiarybutyl for "lower-alkyl" and methoxy, ethoxy, propoxy, isopropoxy, butoxy, isobutoxy and tertiary-butoxy for "lower-alkoxy", the radical $C_nH_{2n}$, where n is an integer from 2 to 4, represents alkylene, which can be straight or branched, as illustrated by, but not limited to, —$CH_2CH_2$—, —$CH_2CH_2CH_2$—, —$CH(CH_3)CH_2$—, —$CH(CH_3)CH(CH_3)$—, and —$CH_2CH_2CH_2CH_2$—, and the term "halo" means chloro, fluoro and iodo.

Throughout this specification where $C_nH_{2n}NR_1R_2$ comprehends heterocyclic rings substituted on carbon by from one to three lower-alkyl substituents, the lower-alkyl substituents can be attached to any available ring carbon atom, and such rings are illustrated by, but not limited to, 2-methyl-1-piperidyl, 4-methyl-1-piperidyl, 3-ethyl-1-piperidyl, 2,6-dimethyl-1-piperidyl, 2,4-dimethyl-1-piperidyl, 2,4,6-trimethyl-1piperidyl, 3-propyl-1-piperidyl, 2,5-dimethyl-1-pyrrolidyl, 2,3-dimethyl-4-morpholinyl, 2-ethyl-4-morpholinyl, 3-ethyl-1-piperazinyl and 2,4,6-trimethylpiperazinyl.

The compounds as illustrated by the compounds of formula I, are useful both in the free base form and in the form of acid-addition salts, and both forms are within the purview of the invention. The acid-addition salts are simply a more convenient form for use, and in practice, use of the salt form inherently amounts to use of the base form. For pharmaceutical purposes, the acids which can be used to prepare the acid-addition salts include preferably those which produce, when combined with the free base, medicinally acceptable salts, that is, salts whose anions are relatively innocuous to the animal organism in medicinal doses of the salts, so that the beneficial properties inherent in the free base are not vitiated by side effects ascribable to the anions. Appropriate medicinally acceptable salts within the scope of the invention are those derived from mineral acids such as hydrochloric acid, hydrobromic acid, hydroiodic acid, nitric acid, phosphoric acid, sulfamic acid, and sulfuric acid; and organic acids such as acetic acid, citric acid, tartaric acid, lactic acid, cyclohexanesulfamic acid, methanesulfonic acid, ethanesulfonic acid, benzenesulfonic acid, p-toluenesulfonic acid, quinic acid, and the like, giving the hydrochloride, hydrobromide, hydriodide, nitrate, phosphate, sulfamate, acetate, citrate, tartrate, lactate, cyclohexanesulfamate, methanesulfonate, ethanesulfonate, benzenesulfonate, p-toluenesulfonate and quinate, respectively.

The acid-addition salts of said basic compounds are prepared either by dissolving the free base in aqueous or aqueous-alcohol solution containing the appropriate acid and isolating the salt by evaporating the solution, or by reacting the free base and acid in an organic solvent, in which case the salt separates directly or can be obtained by concentration of the solution.

Although medicinally acceptable salts of said basic compounds are preferred for pharmaceutical purposes, all acid-addition salts are within the scope of our invention. All acid-addition salts are useful as sources of the free base form even if the particular salt per se is desired only as an intermediate product as for example when the salt is formed only for purposes of purification or identification, or when it is used as an intermediate in preparing a medicinally acceptable salt by ion exchange procedures.

The compounds of formula I of this invention possess useful pharmacological properties as determined by standard test procedures described hereinbelow. Thus they possess useful antifertility and hypocholesterolemic activities. The actual determination of the numerical biological data definitive for a particular compound, for each type of activity, is readily determined by standard test procedures by technicians having ordinary skill in pharmacological test procedures, without the need for any extensive experimentation.

The compounds can be prepared for use by dissolving under sterile conditions salt forms of the compounds in water (or an equivalent amount of a non-toxic acid if the free base is used), or in a physiologically compatible aqueous medium such as saline, and stored in ampoules for intramuscular injection. Alternatively, they can be incorporated in unit dosage form as tablets or capsules for oral adminstration either alone or in combination with suitable adjuvants such as calcium carbonate, starch, lactose, talc, magnesium stearate, gum acacia, and the like. Still further the compounds can be formulated for oral administration in aqueous alcohol, propylene glycol, or oil solutions or oil-water emulsions in the same manner as conventional medicinal substances are prepared.

The novel compounds of formulas II and III above are useful as intermediates for the preparation of the novel compounds of formula I.

The compounds of formula I ($R_4 \neq OH$) are prepared by reacting an alkali-metal salt of an appropriate 1-(4-hydroxyphenyl)indole (II, $R_5=H$) with an appropriate amino-lower-alkyl halide of the formula $Y-C_nH_{2n}NR_1R_2$ (IX), where Y is chloro, bromo or iodo. In this reaction, the indole II ($R_5=H$) cannot bear a 5-hydroxyl substituent ($R'_4 \neq OH$) since that substituent would also be subject to alkylation with the amino-lower-alkyl halide. The compounds of formula I where $R_4$ is hydroxy are prepared by ester hydrolysis of the corresponding compounds where $R_4$ is benzoyloxy. The 1-(4-hydroxyphenyl)indole (II, $R_5=H$) is obtained by reacting an appropriate cyclohexanone with pyrrolidine, treating the so obtained cyclohexenylamine with an appropriate 2-bromoacetophenone, reacting the resulting oxocyclohexylacetophenone with 4-hydroxy or 4-benzyloxyaniline and dehydrogenating the resulting 4,5,6,7-tetrahydroindole (III) to give the indole II ($R_5=H$ or benzyl). The reaction of the oxocyclohexylacetophenone with 4-benzyloxyaniline and dehydrogenation of the corresponding tetrahydroindole (III, $R_5=$benzyl) are preferred for preparing the indole II where $R'_4$ is benzoyloxy, the benzyl substituent serving as a protective group to prevent undesirable side reactions with the benzoyloxy ester during these reactions. The 1-(4-benzyloxyphenyl)indole II ($R_5=$benzyl) can be converted to the corresponding indole (II, $R_5=H$) by reductive cleavage of the benzyl ether.

The foregoing reaction steps are illustrated by the following equations:

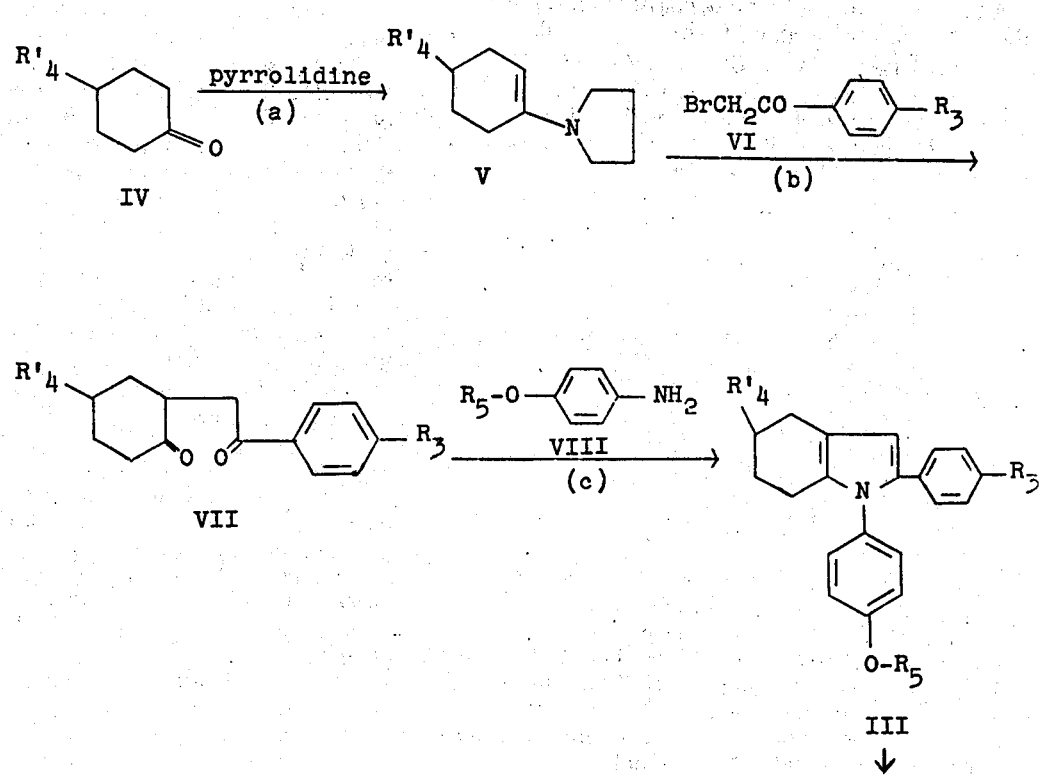

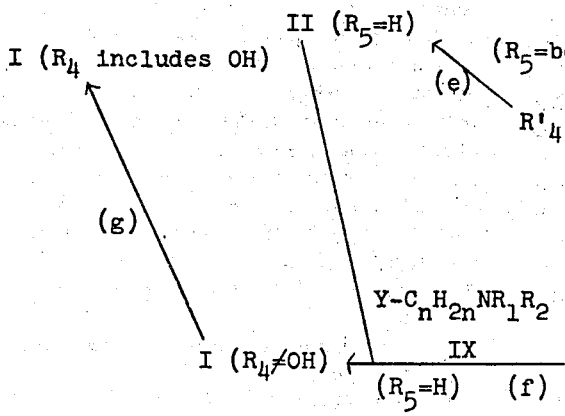
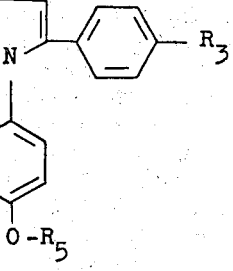

In the above illustrated reaction steps, $R_1$, $R_2$, $R_3$, $R_4$, $R'_4$, $R_5$, $n$ and Y have the meanings defined hereinbefore, except where otherwise indicated.

Step (a) is accomplished by heating the cyclohexanone IV with excess pyrrolidine in a suitable solvent. The reaction is conveniently carried out in benzene at reflux temperature with azeotropic removal of the water formed until the stoicheometric amount of water has been collected. The cyclohexanones IV belong to a class of known compounds and are readily prepared from the corresponding cyclohexanols by a standard oxidative procedure i.e., reaction with sodium dichromate in water in the presence of sulfuric acid. The cyclohexanols in turn are prepared from the corresponding known phenols by a standard hydrogenation procedure i.e., subjecting the phenol in ethyl alcohol to a hydrogen atmosphere at about 1500 pounds per square inch gauge and at about 90°–100°C. in the presence of alkali-free Raney nickel. Step (b) is accomplished by reacting the cyclohexenylamine V with an equivalent of the 2-bromoacetophenone VI in a suitable solvent at elevated temperature. The reaction is conveniently carried out in toluene at reflux temperature for about 1 to 3 hours. The 2-bromoacetophenones (VI) belong to a class of well-known compounds and are readily prepared from the known corresponding acetophenones by standard bromination procedures. A convenient procedure involves adding bromine in chloroform dropwise to a solution of the appropriate acetophenone in chloroform at about 2°C. and stirring the resulting solution for about 3 to 4 hours. The resulting 2-bromoacetophenone can be isolated and purified using standard procedures. Step (c) is accomplished by reacting the oxocyclohexylacetophenone VII with an equivalent of the aniline VIII in glacial acetic acid. The reaction is conveniently carried out at reflux temperature for about one-half hour. The anilines VIII are known compounds. Step (d) is carried out by heating the 4,5,6,7-tetrahydroindole III in a suitable solvent in the presence of palladium-on-charcoal at an appropriate temperature adequate to affect aromatization. The reaction is conveniently carried out in mesitylene at reflux temperature in a nitrogen atmosphere in the presence of 10% palladium-on-charcoal for from three hours to three days. Step (e) is accomplished by subjecting the indole II ($R_5$=benzyl) in ethyl alcohol to a hydrogen atmosphere at about 50 to 60 pounds per square inch gauge over 10% palladium-on-charcoal catalyst at room temperature until the stoichiometric amount of hydrogen has reacted. Step (f) is accomplished by preparing an alkali-metal salt of the indole II ($R_5$=H) in a suitable solvent, adding the amino-lower-alkyl halide IX, in a suitable solvent if desired, and heating the reaction mixture. The reaction is conveniently carried out by reacting a solution of the indole II ($R_5$=H) in chlorobenzene with a slight excess of sodium methoxide at reflux temperature with distillation of part of the solvent, cooling the mixture containing the sodium salt of the indole, adding an amount, equivalent to the amount of sodium methoxide used, of the amino-lower-alkyl halide, neat or as a solution in benzene or chlorobenzene, and heating under reflux for about 4 hours. The amino-lower-alkyl halides (IX) are commercially available compounds or can be prepared by standard preparative methods. Step (g) is carried out by dissolving the indole I ($R_4$=benzoyloxy) in aqueous ethyl alcohol containing an excess of sodium hydroxide and refluxing for about one-half to one hour and isolating the product by standard procedures.

The compounds of formula I where $R_4$ is lower-alkoxy can also be prepared by reacting the alkali-metal salt of the corresponding indole (I, $R_4$=OH) with an appropriate lower-alkyl halide i.e., chloride, bromide or iodide, using a procedure similar to that described above for step (f). The lower-alkyl halides are commercially available compounds or are readily prepared by standard preparative methods.

TEST PROCEDURE FOR THE DETERMINATION OF ANTIFERTILITY ACTIVITY

Mature female rats were medicated daily with the test agent for 6 days after insemination by proven male rats (a total of six medications). The rats were autopsied 15 days after insemination and their uteri were removed and examined for evidence of pregnancy. The test agents were administered either as suspensions, depending on solubility and dosage level, in 10 percent ethyl alcohol-cottonseed oil.

The compounds of formula I of this invention were found to be effective as antifertility agents, completely preventing pregnancy when administered either subcutaneously or orally to female rats in the dose range of from 2 to 25 mg/kg × 6 days (calculated on the basis of the free base) according to the procedure described above. Thus, they are indicated for use as antifertility agents.

TEST PROCEDURE FOR THE DETERMINATION OF HYPOCHOLESTEROLEMIC ACTIVITY

Male rats were fasted for 5 hours, medicated with the test agent in gum tragacanth via stomach tube and then fed. This regimen was continued four days. A control group of male rats was subjected to the same regimen except that they were not medicated with the test agent. On the fifth day, blood was taken by cardiac puncture and serum samples were analyzed for cholesterol. The test agents were considered to have hypocholesterolemic activity if there was a significant decrease (>15%) in the serum cholesterol level of the medicated rats from that of the control rats.

The compounds of formula I were found to effectively decrease serum cholesterol levels by from 43 to 80% when administered by gavage to male rats at a dose of 256 mg/kg × 4 days according to the above test procedure. Thus, they are indicated for use as hydrocholesterolemic agents, that is, as agents for lowering blood cholesterol levels.

The molecular structures of the compounds of this invention were assigned on the basis of the method of their synthesis and study of their infrared spectra, and confirmed by the correspondence between calculated and found values for the elementary analysis for representative examples.

The following examples will further illustrate the invention:

EXAMPLE 1

1-{4-[2-(Diethylamino)ethoxy]phenyl}-5-methoxy-2-phenylindole

A. N-(4-Methoxy-1-cyclohexenyl)pyrrolidine

A solution of 85.4 g. of 4-methoxycyclohexanone and 83.3 ml. of pyrrolidine in 500 ml. of benzene was heated under reflux for four hours during which time the water formed was separated by means of a water trap. The mixture was concentrated, toluene was added, and the mixture was distilled until no pyrrolidine was detected in the distillate. This solution of crude N-(4-methoxy-1-cyclohexenyl)pyrrolidine was used in step 3.

B. 2-(5-Methoxy-2-oxocyclohexyl)acetophenone

A solution of N-(4-methoxy-1-cyclohexenyl)pyrrolidine (0.65 mole) and 130 g. of 2-bromoacetophenone in 600 ml. of toluene was heated under reflux with stirring for 3 hours and cooled. The crude hydrobromide salt of the pyrrolidine enamine of 2-(2-oxocyclohexyl)acetophenone was filtered, dissolved in 250 ml. of water and the solution was warmed on a steambath. The resulting brown oily layer was extracted into chloroform, dried, and the extract was concentrated under reduced pressure to give 130 g. of a brown oil, distillation of 98.8 g. of which yielded 57.6 g. of 2-(5-methoxy-2-oxocyclohexyl)acetophenone; b.p. 171°–177°C. (0.05–0.06 mm).

C. 1-(4-Hydroxyphenyl)-5-methoxy-2-phenyl-4,5,6,7-tetrahydroindole

A solution of 24.63 g. of 2-(5-methoxy-2-oxocyclohexyl)acetophenone and 10.9 g. of 4-aminophenol in 60 ml. of glacial acetic acid was heated under reflux for one-half hour, diluted with 30 ml. of water and cooled. The crystals were filtered, washed with water and recrystallized from methyl alcohol to give 27.4 g. of 1-(4-hydroxyphenyl)-5-methoxy-2-phenyl-4,5,6,7-tetrahydroindole; m.p. 174°–175°C.

D. 1-(4-Hydroxyphenyl)-5-methoxy-2-phenylindole

To a solution of 27.4 g. of 1-(4-hydroxyphenyl)-5-methoxy-2-phenyl-4,5,6,7-tetrahydroindole in 500 ml. of mesitylene was added 20 g. of 10% palladium-on-charcoal and the mixture was heated under reflux in a nitrogen atomosphere for 3 days, filtered hot and concentrated. The resulting crystals were filtered and recrystallized first from chloroform-carbontetrachloride and then from isopropyl alcohol to give 14.1 g. of 1-(4-hydroxyphenyl)-5-methoxy-2-phenylindole; m.p. 200°–201°C.

E. 1-{4-[2-(Diethylamino)ethoxy]phenyl}-5-methoxy-2-phenylindole

A stirred mixture of 10.6 g. of 1-(4-hydroxyphenyl)-5-methoxy-2-phenylindole in 150 ml. of chlorobenzene and 2.2 g. of sodium methoxide in 10 ml. of methyl alcohol was distilled until 20 ml. of distillate had been collected, cooled, and 16 ml. of a 2.5-N solution of N-(2-chloroethyl)diethylamine in toluene was added and mixture was heated under reflux with stirring for 4 hours and 5 ml. of 35% sodium hydroxide and 80 ml. of water was added to the warm mixture and stirring was continued for one-half hour. The layers were separated, the aqueous layer was extracted with ether and the combined organic solutions were dried and concentrated to dryness under reduced pressure to give 14 g. of crude product. To a warm solution of 13 g. of this crude base in 30 ml. isopropyl alcohol was added a solution of p-toluenesulfonic acid monohydrate in 18 ml. of isopropyl alcohol and 100 ml. ether was slowly added. The resulting crystals were filtered to give, after recrystallization from isopropyl alcohol-ether, 8.1 g. of 1-{4-[2-(diethylamino)ethoxy]phenyl}-5-methoxy-2-phenylindole p-toluenesulfonate; m.p. 131°–132°C.

Preparation of 4-Methoxycyclohexanone — intermediate for Example 1A

A solution of 496.52 g. (4mole) of 4-methoxypenol in 400 m. absolute ethyl alcohol was subjected to a hydrogen atmosphere in the presence of 60 g. alkali-free Raney nickel at 1800 p.s.i.g. and about 90°C. When the uptake of hydrogen was completed (about 2 hours) the mixture was filtered, concentrated and the residue was distilled to give 360 g. of liquid; b.p. 101°–110°C. (11–12 mm); redistillation of 230 g. of this liquid yielded 160.1 g. of 4-methoxycyclohexanol; b.p. 96°–100°C. (8.5 mm); $n_D^{25}$ 1.4681. 4-Methoxycyclohexanol (130.18 g.; 1mole) was added to a stirred solution of 20 g. of sodium dichromate dihydrate (0.69 mole) in sulfuric acid (prepared by adding 93.5 ml. of concentrated sulfuric acid to 1 liter of water) at 0°C. The reaction temperture rsoe to 20°C., slight warming was applied and the temperature rose to 70°C. and stirring was continued for 1 hour. The mixture was cooled, extracted with methylene dichloride and ether and the extracts were dried and concentrated to give 90 g. of liquid, distillation of which gave 48.8 g. of 4-methoxycyclohexanone; b.p. 80°–82°C. (7.5 mm).

The 4-R'$_4$-cyclohexanones (IV), intermediates for the preparation of the compounds of the invention, can be prepared using the above-described procedures, but substituting for 4-methoxyphenol an equivalent amount of appropriately 4-substituted phenols.

EXAMPLE 2

1-{4-[2-(Diethylamino)ethoxy]phenyl}-2-phenylindole

A. N-(1-Cyclohexenyl)pyrrolidine

Following a precedure similar to that of Example 1A but using 392 g. of cyclohexanone and 533 ml. of pyrrolidine in 800 ml. benzene there was obtained, on evaporation to dryness of the reaction solution and distillation of the residue, 495 g. of N-(1-cyclohexenyl)pyrrolidine; b.p. 70°–72°C. (0.5–1 mm).

B. 2-(2-Oxocyclohexyl)acetophenone

Following a procedure similar to that of Example 1B but using 403 g. of N-(1-cyclohexenyl)pyrrolidine and 530 g. of 2-bromoacetophenone in 1 liter of toluene there was obtained 245 g. of 2-(2-oxocyclohexyl)acetophenone; b.p. 160°–167°C. (0.8–1.7 mm).

C. 1-(4-Hydroxyphenyl)-2-phenyl-4,5,6,7-tetrahydroindole

Following a procedure similar to that of Example 1C but using 216.3 g. of 2-(2-oxocyclohexyl)acetophenone and 109.1 g. of 4-aminophenol in 650 ml. glacial acetic acid there was obtained 227 g. of 1-(4-hydroxyphenyl)-2-phenyl-4,5,6,7-tetrahydroindole; m.p. 181°–182°C. (isopropyl alcohol).

D. 1-(4-Methoxyphenyl)-2-phenyl-4,5,6,7-tetrahydroindole

Following a procedure similar to that of Example 1C but using 64.9 g. of 2-(2-oxocyclohexyl)acetophenone and 37 g. of 4-methoxyaniline in 180 ml. glacial acetic acid there was obtained 80.9 g. of 1-(4-methoxyphenol)-2-phenol-4,5,6,7-tetrahydroindole; m.p. 132°–133°C. (isopropyl alcohol).

E. 1-(4-Methoxyphenyl)-2-phenylindole

Following a procedure similar to that of Example 1D but using 63 g. of 1-(4-methoxyphenyl)-2-phenyl-4,5,6,7-tetrahydroindole and 18 g. of 10% palladium-on-charcoal in 600 ml. mesitylene (18 hours reflux) there was obtained, on recrystallization first from isopropyl alcohol and then from tetrahydrofuran-hexane, 58.5 g. of 1-(4-methoxyphenyl)-2-phenylindole; m.p. 141°–142°C.

F. 1-(4-Hydroxyphenyl)-2-phenylindole

Following a procedure similar to that of Example 1D but using 202 g. of 1-(4-hydroxyphenyl)-2-phenyl-4,5,6,7-tetrahydroindole and 35 g. of 10% palladium-on-charcoal in 1900 ml. of mesitylene (6 hours reflux) there was obtained, on recrystallization from benzene-cyclohexane, 157 g. of 1-(4-hydroxyphenyl)-2-phenylindole; m.p. 137°C. Recyrstallization of a small sample from benzene-cyclohexane raised the melting point to 139°–140°C.. Alternatively this compound can be prepared by demethylation of 1-(4-methoxyphenyl)-2-phenylindole by heating an acetic acid solution thereof containing an excess of 30% hydrogen bromide at reflux in a nitrogen atmosphere for about 5 hours and isolating the product using standard isolation procedures.

G. 1-{4-(Diethylamino)ethoxy]phenyl}-2-phenylindole

Following a procedure similar to that of Example 1E but using 28.53 g. of 1-(4-hydroxyphenyl)-2-phenylindole, 300 ml. of chlorobenzene, 5.45 g. of sodium methoxide in 68 ml. dry methyl alcohol, and 15 g. of N-(2-chloroethyl)diethylamine there was obtained 35 g. of crude product, 32 g. of which was converted to 30.1 g. of 1-{4-[2-(diethylamino)ethoxy]phenyl}-2-phenylindole p-toluenesulfonate; m.p. 123°–124°C.

(isopropyl alcohol). A solution of the free base in chloroform was shaken with a slight excess of concentrated hydrochloric acid in water, the layers were separated, dried and concentrated. The residue was dissolved in isopropyl alcohol, concentrated, and diluted with ethyl acetate. The resulting solids were filtered to give 1-{4-[2-(diethylamino)ethoxy]phenyl}-2-phenylindole hydrochloride; m.p. 154°–155°C.

EXAMPLE 3

1-{4-[2-(1-Pyrrolidyl)ethoxy]phenyl}-2-phenylindole

Following a procedure similar to that of Example 1E but using 28.53 g. of 1-(4-hydroxyphenyl)-2-phenylindole, 300 ml. of chlorobenzene, 5.5 g. of sodium methoxide in 50 ml. of dry methyl alcohol, and N-(2-chloroethyl)pyrrolidine in 100 ml. of chlorobenzene there was obtained 36 g. of crude product, a solution of 35 g. of which was dissolved in hot acetone, treated with a solution of 18 g. of cyclohexanesulfamic acid, diluted with 200 ml. of ether to give, on recrystallization from isopropyl alcohol, 25.8 g. of 1-{4-[2-(1-pyrrolidyl)ethoxy]-phenyl}-2-phenylindole cyclohexane sulfamate; m.p. 152.5°–153.5°C.

EXAMPLE 4

A. N-(4-Benzoyloxy-1-cyclohexenyl)pyrrolidine

Following a procedure similar to that of Example 1A but using 21.82 g. of 4-benzyloxycyclohexanone and 12.5 ml. of pyrrolidine in 200 ml. of benzene there was obtained a toluene solution of crude N-(4-benzoyloxy-1-cyclohexenyl)-pyrrolidine which was used in the next step.

B. 2-(5-Benzoyloxy-2-oxocyclohexyl)acetophenone

Following a procedure similar to that described in Example 2A but using N-(4-benzoyloxy-1-cyclohexyl)-pyrrolidine (0.1 mole) and 20 g. of 2-bromoacetophenone in 100 ml. of toluene there was obtained 25.4 g. of 2-(5-benzoyloxy-2-oxocyclohexyl)acetophenone; m.p. 107°–108°C. (methyl alcohol).

C. 1-(4-Benzyloxyphenyl)5-benzoyloxy-2-phenyl-4,5,6,7-tetrahydroindole

Following a procedure similar to that described for Eample 1C but using 13.5 g. of 2-(5-benzoyloxy-2-oxocyclohexyl)acetophenone and 8 g. of 4-benzyloxyaniline in 40 ml. of glacial acetic acid there was obtained, after recrystallizations from isopropyl alcohol and benzene-cyclohexane, 16.2 g. of 1-(4-benzyloxyphenyl)-5-benzoyloxy-2-phenyl-4,5,6,7-tetrahydroindole; m.p. 124°–125°C.

Following a procedure similar to that described in Example 1D but substituting for 1-(4-hydroxyphenyl)-5-methoxy-2-phenyl-4,5,6,7-tetrahydroindole and equivalent amount of 1-(4-benzyloxyphenyl)-5-benzolyloxy-2-phenyl-4,5,6,7-tetrahydroindole there can be obtained 1-(4-benzyloxyphenyl)-5-benzolyloxy-2-phenylindole.

By subjecting 1-(4-benzyloxyphenyl)-5-benzoyloxy-2-phenylindole to the standard debenzylation procedure described hereinbefore there can be obtained 1-(4-hydroxyphenyl)-5-benzoyloxy-2-phenylindole.

Following a procedure similar to that described in Example 1E but substituting for 1-(4-hydroxyphenyl)-5-methoxy-2-phenylindole an equivalent amount of 1-(4-hydroxyphenyl)-5-benzoyloxy-2-phenylindole there can be obtained 1-{4-[2-(diethylamino)ethoxy]-phenyl}-5-benzoyloxy-2-phenylindole.

By subjecting 1-{4-[2-(diethylamino)ethoxy]phenyl}-5-benzoyloxy-2-phenylindole to the standard ester hydrolysis procedure described hereinbefore there can be obtained 1-{4-[2-(diethylamino)ethoxy]phenyl}-5-hydroxy-2-phenylindole.

Following a procedure similar to that of Example 1E but substituting for N-(2-chloroethyl)diethylamine an equivalent amount of
N-(2-chloroethyl)diisopropylamine,
N-(2-chloroethyl)morpholine,
N-(2-chloroethyl)thiomorpholine,
N-(2-chloromethyl)piperidine,
N-(2-chloroethyl)piperazine,
N-(2-chloroethyl)-N'-methylpiperazine,
N-(2-chloroethyl)-N'-phenylpiperazine,
N-(2-chloro-1,2-dimethylethyl)dimethylamine,
N-(2-chloropropyl)-N-ethyl-N-methylamine, and
N-(4-chlorobutyl)dimethylamine
there can be obtained, respectively,
1-{4-[2-(diisopropylamino)ethoxy]phenyl}-5-methoxy-2-phenylindole,
1-{4-(4-morpholinyl)ethoxy]phenyl}-5-methoxy-2-phenylindole,
1-{4-[2-(4-thiomorpholinyl)ethoxy]phenyl}-5-methoxy-2-phenylindole,
1-{4-[2-(1-piperidyl)ethoxy]phenyl}-5-methoxy-2-phenylindole,
1-{4-[2-(1-piperazinyl)ethoxy]phenyl}-5-methoxy-2-phenylindole,
1-{4-[2-(4-methyl-1-piperazinyl)ethoxy]phenyl}-5-methoxy-2-phenylindole,
1-{4-[2-(4-phenyl-1-piperazinyl)ethoxy]phenyl}-5-methoxy-2-phenylindole,
1-{4-[2-(dimethylamino)-1,2-dimethylethoxy]phenyl}-5-methoxy-2-phenylindole,
1-{4-[2-(N-ethyl-N-methylamino)-1-methylethoxy]phenyl}-5-methoxy-2-phenyindole, and
1-{4-(dimethylamino)butoxy]phenyl}-5-methoxy-2-phenylindole.

Following a procedure similar to that of Example 1A but substituting for 4-methoxycyclohexanone and equivalent amount of
4-methylcyclohexanone,
4-isopropylcyclohexanone,
4-butylcyclohexanone,
4-propoxycyclohexanone, and
4-tert-butoxycyclohexanone
there can be obtained, respectively,
N-(4-methyl-1-cyclohexenyl)pyrrolidine,
N-(4-isopropyl-1-cyclohexenyl)pyrrolidine,
N-(4-butyl-1-cyclohexenyl)pyrrolidine,
N-(4-propoxy-1-cyclohexenyl)pyrrolidine, and
N-(4-tert-butoxy-1-cyclohexenyl)pyrrolidine.

Following a procedure similar to that of Example 1B but substituting for N-(4-methoxy-1-cyclohexenyl)pyrrolidine an equivalent amount of the pyrrolidines listed in the previous paragraph, and for 2-bromoacetophenone respectively an equivalent amount of the following,
4'-chloro-2-bromoacetophenone,
4'-methoxy-2-bromoacetophenone,
4'-butyl-2-bromoacetophenone,
4'-fluoro-2-bromoacetophenone, and
4'-methyl-2-bromoacetophenone,
there can be obtained, respectively,
2-(5-methyl-2-oxocyclohexyl)-4'-chloroacetophenone,
2-(5-isopropyl-2-oxocyclohexyl)-4'-methoxyacetophenone,
2-(5-butyl-2-oxocyclohexyl)-4'-butylacetophenone,
2-(5-propoxy-2-oxocyclohexyl)-4'-fluoroacetophenone, and
2-(5-tert-butoxy-2-oxocyclohexyl)-4'-methylacetophenone.

The above-named 2-bromoacetophenones can be prepared from the corresponding known acetophenones following the general procedure described hereinbefore.

Following a procedure similar to that of Example 1B but substituting for 2-bromoacetophenone an equivalent amount of
2-bromo-4'-bromoacetophenone,
2-bromo-4'-tert-butoxyacetophenone,
2-bromo-4'-ethoxyacetophenone, and
2-bromo-4'-isopropylacetophenone
there can be obtained, respectively,
2-(5-methoxy-2-oxocyclohexyl)-4'-bromoacetophenone,
2-(5-methoxy-2-oxocyclohexy)-4'-tert-butoxyacetophenone,
2-(5-methoxy-2-oxocyclohexyl)-4'-ethoxyacetophenone, and
2-(5-methoxy-2-oxocyclohexyl)-4'-isopropylacetophenone.

The above-named 2-bromoacetophenones can be prepared from the corresponding known acetophenones following the general procedure described hereinbefore.

Following a procedure similar to that of Example 1C but substituting for 2-(5-methoxy-2-oxocyclohexyl)acetophenone an equivalent amount of the cyclohexylacetophenones listed in the previous two paragraphs there can be obtained, respectively,
1-(4-hydroxyphenyl)-5-methyl-2-(4-chlorophenyl-4,5,6,7-tetrahydroindole,
1-(4-hydroxyphenyl)-5-isopropyl-2-(4-methoxyphenyl-4,5,6,7-tetrahydroindole,
1-(4-hydroxyphenyl)-5-butyl-2-(4-butylphenyl)-4,5,6,7-tetrahydroindole,
1-(4-hydroxyphenyl)-5-propoxy-2-(4-fluorophenyl)-4,5,6,7-tetrahydroindole,
1-(4-hydroxyphenyl)-5-tert-butoxy-2-(4-methylphenyl)-4,5,6,7-tetrahydroindole,
1-(4-hydroxyphenyl)-5-methoxy-2-(4-bromophenyl)-4,5,6,7-tetrahydroindole,
1-(4-hydroxyphenyl)-5-methoxy-2-(4-tert-butoxyphenyl)-4,5,6,7-tetrahydroindole,
1-(4-hydroxyphenyl)-5-methoxy-2-(4-ethoxyphenyl)-4,5,6,7-tetrahydroindole, and
1-(4-hydroxyphenyl)-5-methoxy-2-(4-isopropylphenyl)-4,5,6,7-tetrahydroindole.

Following a procedure similar to that of Example 1D but substituting for 1-(4-hydroxyphenyl)-5-methoxy-2-phenyl-4,5,6,7-tetrahydroindole and equivalent amount of the tetrahydroindoles listed in the previous paragraph there can be obtained, respectively,
1-(4-hydroxypheny)-5-methyl-2-(4-chlorophenyl)indole,
1-(4-hydroyphenyl)-5-isopropyl-2-(4-methoxyphenyl)indole,
1-(4-hydroxyphenyl)-5-butyl-2-(4-butylphenyl)indole,
1-(4-hydroxyphenyl)-5-propoxy-2-(4-fluorophenyl)indole,
1-(4-hydroxyphenyl)-5-tert-butoxy-2-(4-methylphenyl)indole,
1-(4-hydroxyphenyl)-5-methoxy-2-(4-bromophenyl)indole,
1-(4-hydroyphenyl)-5-methoxy-2-(4-tert-butoxyphenyl)indole,
1-(4-hydroxyphenyl)-5-methoxy-2-(4-ethoxyphenyl)indole, and
1-(4-hydroxyphenyl)-5-methoxy-2-(4-isopropylphenyl)indole.

Following a procedure similar to that of Example 1E but substituting for 1-(4-hydroxyphenyl)-5-methoxy-2phenylindole an equivalent amount of the indoles listed in the previous paragraph there can be obtained, respectively, 1-{4-[2-(diethylamino)ethoxy]phenyl}-5-methyl-2-(4-chlorophenyl)indole,
1-{4-[2-(diethylamino)ethoxy]phenyl}-5-isopropyl-2-(4-methoxyphenyl)indole,
1-{4-[2-(diethylamino)ethoxy]phenyl}-5-butyl-2-(4 1butylphenyl)indole,
1-{4-[2-Idiethylamino)ethoxy]phenyl}-5-propoxy-2-(4-fluorophenyl)indole,
1-{4-[2-(diethylamino)ethoxy]phenyl}-5-tert-butoxy-2-(4-methylphenyl)indole,
1-{4-[2-(diethylamino)ethoxy]phenyl}-5-methoxy-2-(4-bromophenyl)indole,
1-{4-[2-(diethylamino)ethoxy]phenyl}-5-methoxy-2-(4-tertbutoxyphenyl)indole,
1-{4-[2-(diethylamino)ethoxy]pheny}-5-methoxy-2-(4-ethoxyphenyl)indole, and
1-{4-[2-(diethylamino)ethoxy]phenyl}-5-methoxy-2-(4-isopropylphenyl)indole.

We claim:
1. A compound of the formula

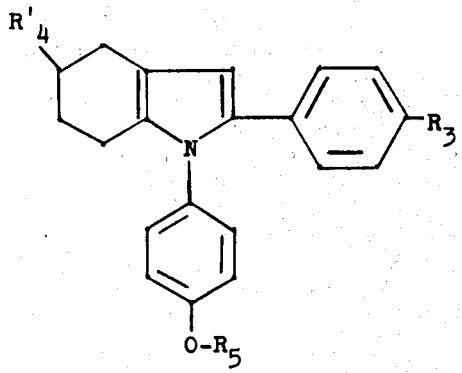

where $R_3$ is hydrogen, lower-alkyl, lower-alkoxy or halo;
$R'_4$ is hydrogen, lower-alkyl, lower-alkoxy or benzoyloxy; and $R_5$ is hydrogen or benzyl.

2. A compound of the formula

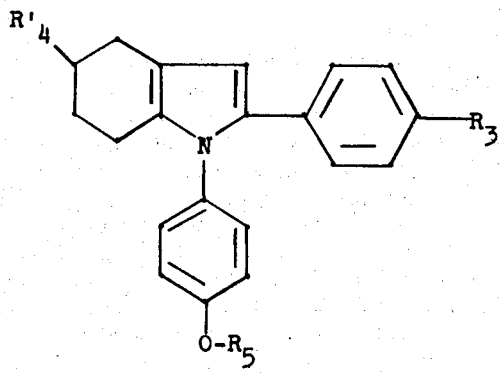

where
$R_3$ is hydrogen or lower-alkyl;
$R'_4$ is hydrogen, lower-alkyl, lower-alkoxy or benzoyloxy; and $R_5$ is hydrogen or benzyl.

3. A compound according to claim 2 where $R'_4$ is hydrogen, lower-alkyl or lower-alkoxy; and $R_5$ is hydrogen.

4. 1-(4-Hydroxyphenyl)-5-methoxy-2-phenyl-4,5,6,7-tetrahydroindole according to claim 3.

5. 1-(4-Hydroxyphenyl)-2-phenyl-4,5,6,7-tetrahydroindole according to claim 3.

6. A compound according to claim 2 where $R'_4$ is benzoyloxy; and $R_5$ is benzyl.

7. 1-(4-Benzyloxphenyl)-5-benzoyloxy-2-phenyl-4,5,6,7-tetrahydroindole according to claim 6.

* * * * *

UNITED STATES PATENT AND TRADEMARK OFFICE
CERTIFICATE OF CORRECTION

PATENT NO. : 3,968,121
DATED : July 6, 1976
INVENTOR(S) : Malcolm R. Bell and Andrew W. Zalay It is certified that error appears in the above-identified patent and that said Letters Patent are hereby corrected as shown below:

Column 1, line 3, "This a division," should read -- This is a division --.

Column 2, line 31, -- bromo, -- should be inserted after -- chloro, --.

Column 2, line 39, "1piperidyl" should read -- 1-piperidyl --.

Column 2, line 60, "hydroiodic" should read -- hydriodic --.

Column 7, lines 19-20, "hydrocholesterolemic" should read -- hypocholesterolemic --.

Signed and Sealed this

Thirtieth Day of November 1976

[SEAL]

Attest:

RUTH C. MASON
Attesting Officer

C. MARSHALL DANN
Commissioner of Patents and Trademarks